(12) United States Patent
Meunier et al.

(10) Patent No.: US 8,470,030 B2
(45) Date of Patent: Jun. 25, 2013

(54) DEVICE FOR LOADING AN INTRAOCULAR LENS INTO AN INJECTION CARTRIDGE

(75) Inventors: Patrick Meunier, Hennebont (FR); Jean-Marc Le Pair, Brech (FR)

(73) Assignee: SIFI MedTech Srl, Aci S. Antonio CT (IT)

( * ) Notice: Subject to any disclaimer, the term of this patent is extended or adjusted under 35 U.S.C. 154(b) by 872 days.

(21) Appl. No.: 11/662,865

(22) PCT Filed: Aug. 18, 2005

(86) PCT No.: PCT/FR2005/002096
§ 371 (c)(1),
(2), (4) Date: Mar. 13, 2007

(87) PCT Pub. No.: WO2006/030082
PCT Pub. Date: Mar. 23, 2006

(65) Prior Publication Data
US 2008/0119865 A1 May 22, 2008

(30) Foreign Application Priority Data
Sep. 13, 2004 (FR) .................... 04 09698

(51) Int. Cl.
*A61F 2/16* (2006.01)
*A61F 9/00* (2006.01)
(52) U.S. Cl.
USPC ........................ 623/6.12; 606/107
(58) Field of Classification Search
USPC .............. 206/5.1; 606/107; 623/6.11–6.12, 623/6.18
See application file for complete search history.

(56) References Cited

U.S. PATENT DOCUMENTS

| 4,257,521 | A | * | 3/1981 | Poler .............................. 206/5.1 |
| 4,643,717 | A | * | 2/1987 | Cook et al. ...................... 604/22 |
| 4,862,885 | A | * | 9/1989 | Cumming ..................... 606/107 |
| 5,643,276 | A | * | 7/1997 | Zaleski ......................... 606/107 |
| 5,944,725 | A | | 8/1999 | Cicenas et al. |

(Continued)

FOREIGN PATENT DOCUMENTS

| EP | 1173115 B1 | 7/2003 |
| EP | 1338254 | 8/2003 |

(Continued)

OTHER PUBLICATIONS

Written Opinion of the International Searching Authority (in English and French received by WIPO on Mar. 2, 2006.

(Continued)

*Primary Examiner* — Ryan Severson
*Assistant Examiner* — Ashley Cronin
(74) *Attorney, Agent, or Firm* — Levine Bagade Han LLP (57) ABSTRACT

Disclosed are a device for loading a flexible intraocular lens into an injection cartridge capable of serving as a packaging support, an injection cartridge and a set formed by said loading device and an injection cartridge. The loading device comprises a tubular element (1) having an internal passage (10), said passage comprising a receiving section (11), an intermediate truncated folding section (12) and an end section (13) capable of receiving an injection cartridge detachably, a supporting element (3) mounted in said receiving section, capable of supporting a lens in a non-folded state, and a plunger (5) capable of pushing a lens (9) positioned in the receiving section through the truncated intermediate folding section to fold said lens gradually, then in the receiving chamber of an injection cartridge placed in the end section.

22 Claims, 7 Drawing Sheets

U.S. PATENT DOCUMENTS

| | | |
|---|---|---|
| 6,733,507 B2 | 5/2004 | McNicholas et al. |
| 2003/0195522 A1 | 10/2003 | McNicholas et al. |
| 2004/0117012 A1* | 6/2004 | Vincent ................ 623/6.12 |

FOREIGN PATENT DOCUMENTS

| | | |
|---|---|---|
| WO | WO 99/62436 | 12/1999 |
| WO | WO 00/62713 | 10/2000 |
| WO | WO 03/045285 | 6/2003 |

OTHER PUBLICATIONS

International Search Report mailed on Mar. 6, 2006 by the European Patent Office in counterpart application No. PCT/FR2005/002096.

* cited by examiner

DEVICE FOR LOADING AN INTRAOCULAR LENS INTO AN INJECTION CARTRIDGE

The present invention relates to a device for the loading of a flexible intraocular lens into an injection cartridge. The present invention relates more particularly to a loading device utilized as a packaging support for a flexible intraocular lens before use, as well as to a specific injection cartridge usable with said loading device and a set formed by said loading device and an injection cartridge.

Intraocular lenses (IOL) are used to replace the natural crystalline lens of a cataract-affected eye. The extraction of the natural crystalline lens and its replacement by an intraocular lens are done surgically. With the emergence of the surgical method using phacoemulsification of the lens, it has been proposed to use intraocular lenses made of flexible and foldable material so that they can be inserted in folded form into the eye by means of a little incision. This insertion of the intraocular lens into the eye is generally done by means of an injection system consisting of an either reusable or disposable syringe-type hand injector and a disposable injection cartridge. Classically, the injection cartridge comprises a lens-receiving chamber extended by a cannula, the receiving chamber being formed by two half-tubes connected by a hinge, each tube being provided with a flap for closing the receiving chamber. After a lens has been placed from a sterile packaging into the open chamber by means of an instrument such as a set of forceps, the lens is folded by closing the chamber, and the cartridge is placed in an appropriate injector comprising a cylindrical body in which a piston is mounted so as to be mobile. The intraocular lens folded in the cartridge is then injected mechanically or hydraulically by actuating the piston after the distal end of the cannula has been inserted into the eye.

To facilitate the transfer of the intraocular lens to the lens-injection cartridge, the document EP 1 173 115 has proposed a device for loading a lens into the open receiving chamber of an injection cartridge, the device being formed by a first support system capable of receiving an injection cartridge and of keeping its receiving chamber in an open position and a second support system capable of holding an intraocular lens. The two systems work together to enable the transfer of the cartridge in an open and flat position to the second support system, the second support system being then folded to transfer the intraocular lens into the receiving chamber and enable the cartridge to be removed from the second support by hand. Then the receiving chamber is closed by hand. The two support systems are designed to be disposable and also serve as systems for packaging the cartridge and the lens before use.

The aim of the present invention is to propose a novel device for the loading a flexible intraocular lens into an injection cartridge comprising a receiving chamber for a lens and a cannula, which is simple in its design and use.

To this end, an object of the present invention is a device for the loading of a lens, characterized in that it comprises a tubular element having an internal passage or lumen, said passage comprising a receiving section for receiving a lens in the non-folded state, an intermediate truncated folding section and an end section capable of receiving an injection cartridge detachably so that the truncated intermediate folding section leads into the receiving chamber of the injection cartridge, a supporting element mounted in said receiving section, capable of supporting a lens in a non-folded state, and a plunger comprising a rod that is mounted so as to be movable in the internal passage, capable of pushing a lens positioned in the receiving section through the truncated intermediate folding section to fold said lens gradually, then in the receiving chamber of an injection cartridge placed in the end section.

By means of a simple mechanical thrusting action, the loading device of the invention enables the gradual folding of the flexible intraocular lens, which is initially in the non-folded state, and its direct insertion into an injection cartridge, the folding of the lens requiring no particular manual handling of the cartridge. The loading device of the invention advantageously serves as a packaging support for the lens.

According to one particular feature, the loading device comprises braking means, or retaining means, creating at least resistance to the rearward return of the rod of the plunger in said internal passage, said end section being capable of detachably receiving holding means that extend in the internal passage up to its receiving section to longitudinally block a lens positioned in said receiving section against the free end of the rod of the plunger. Advantageously, said braking means create a blocking of the rearward return of the rod of the plunger in the internal passage and, if necessary, resistance to the forward movement of the rod of the plunger in the internal passage.

According to one embodiment, the internal passage of the tubular element comprises an open distal end by which an injection cartridge is fitted into the cylindrical end section, the tubular element being advantageously provided with a longitudinal slot opening out into said end section and extending up to said distal end to enable the passage of the flap of an injection cartridge. Advantageously, the longitudinal slot is of a bayonet type, so as to enable the blocking of a cartridge in the end section by the engaging of its flap in the longitudinal slot.

According to one embodiment, the internal passage of the tubular element comprises an open proximal end by which the supporting element is fitted into the receiving section, the supporting element being possibly formed by a tip with a head that gets fitted into the receiving section having a cylindrical shape, the tip being provided with a longitudinal slot defining an upper arm and a lower arm between which a lens can be received, said head of the tip presenting a channel that opens out between said arms and in which the rod of the plunger is mounted so as to be mobile. Thus the lens is radially secured between the two arms of the tip and the cylindrical wall of the receiving section.

The loading device advantageously has means for the blocking, in rotation and in translation, of the supporting element in the tubular element. According to one embodiment, the head of the tip, on its external cylindrical wall having a greater diameter than the tip, has a flat surface and a flange is which co-operate respectively with a flat surface and a ring-shaped groove made on the internal wall of a first wide-diameter part of the receiving section.

The braking means of the rod of the plunger comprises, for example, transversal notches, for example formed on a flat surface of the rod, working with a ridge formed in the channel of the head, for example on a flat surface of said channel.

The holding means may include an endpiece comprising a rod capable of getting fitted into the internal passage through the open distal end of said internal passage, and of getting interposed between the two arms of the supporting element to longitudinally block a lens in the receiving section, between the free end of its rod and the free end of the rod of the plunger. In the vicinity of their free end, said rods may include recesses designed to receive the haptic part of an intraocular lens.

Advantageously, said tip has a conical end extending in the truncated folding section of the internal passage, the external faces of the corresponding conical end parts of the arms matching the truncated wall of the folding section, the opposite internal faces of said conical end parts being shaped so as to form guiding surfaces for the folding of the lens. According to one embodiment, the slot of the tip is offset relative to the longitudinal axis of the tip, the conical end part of the lower arm has a concave internal face, the lower conical end part of the upper arm having a convex internal face. For example, the conical end parts of the arms extend in the end section of the tubular element and are capable of getting inserted in the truncated inlet section of the receiving chamber of an injection cartridge placed in said end section.

According to one particular feature, the tubular element comprises side holes opening out into the receiving section, between the arms of the tubular element to enable the passage of sterilizing agent, lubricants and/or a tool to position the haptic part of the lens relative to the rod of the holding endpiece.

The device advantageously comprises supporting surfaces for actuating the plunger, formed by an actuating push-button at the proximal end of the rod of the plunger and two diametrically opposite legs on the external wall of the tubular element, the loading device thus taking the form of a syringe-type device.

The present invention furthermore proposes a loading device, as described here above, loaded with a flexible intraocular lens and packed in a sterile blister.

An object of the invention is also an injection cartridge designed to be loaded with a flexible intraocular lens by means of the above-described loading device, the cartridge comprising a receiving chamber for receiving a lens in folded form extended by a cannula for the injection of the folded lens, wherein the receiving chamber is formed by a single tube. The loading device of the invention, using a simple thrust action for the folding and loading of the lens, enables the use of injection cartridges that have no moving parts and are simple to manufacture.

According to one particular feature, the receiving chamber has a truncated section delimited on one side by the inlet hole of the receiving chamber and extended on the other side by a cylindrical section, said truncated section, designed to receive the conical end parts of the supporting element, enabling the length of the loading device to be reduced. Advantageously, on its outer wall, said tube comprises a rectangular longitudinal flap extending radially outwards, by which it can be blocked on the loading device.

An object of the invention is also a set comprising a loading device as described here above and an injection cartridge, especially a cartridge according to the invention as described here above.

The invention will be understood more clearly and other aims, details, features and advantages shall appear more clearly in the following detailed explanatory description of a particular, currently preferred embodiment of the invention, the description being made with reference to be appended schematic drawings, of which:

FIG. 9 is a view in perspective of the supporting element of the device of FIGS. 1 to 6;

FIG. 10 is a view in perspective of the rod of the plunger of the device of FIGS. 1 to 6;

FIG. 10 is a view in perspective of the holding endpiece of the device of FIGS. 1, 3 and 4;

FIG. 12 is a view in perspective of the cartridge of FIGS. 2, 5 and 6;

The loading device shown in FIGS. 1 to 6 takes the form of a syringe-type device. It comprises a tubular element 1 having an internal passage or lumen 10 with a longitudinal axis A. A lens-supporting element 3 and the rod 51 of a plunger 5 are inserted into this internal passage 10 through its open proximal end 10a and a removable holding endpiece 6 or an injection cartridge 7 is inserted into this internal passage 10 through its open distal end 10b.

Figure 1:
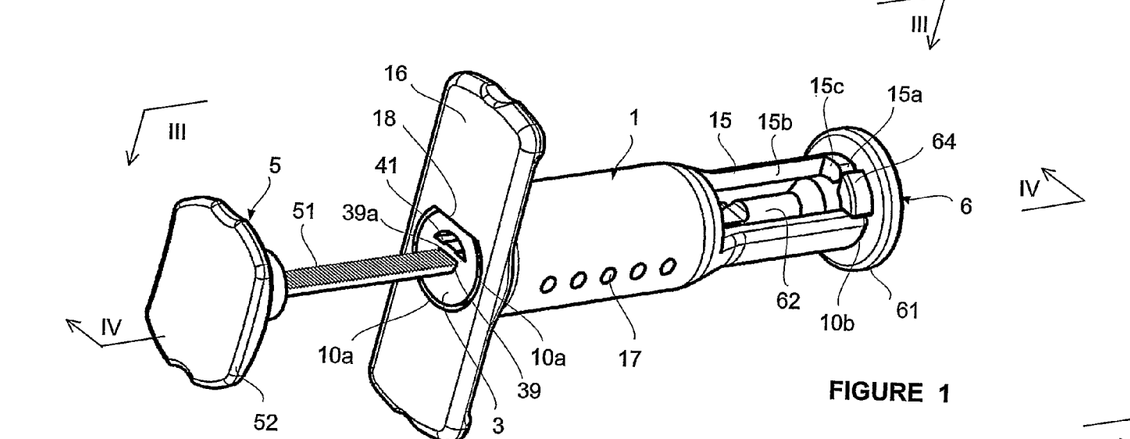
FIG. 1 is a view in perspective of a loading device according to the invention, equipped with a holding endpiece for the storage and transportation of a lens before use.
Figure 2:
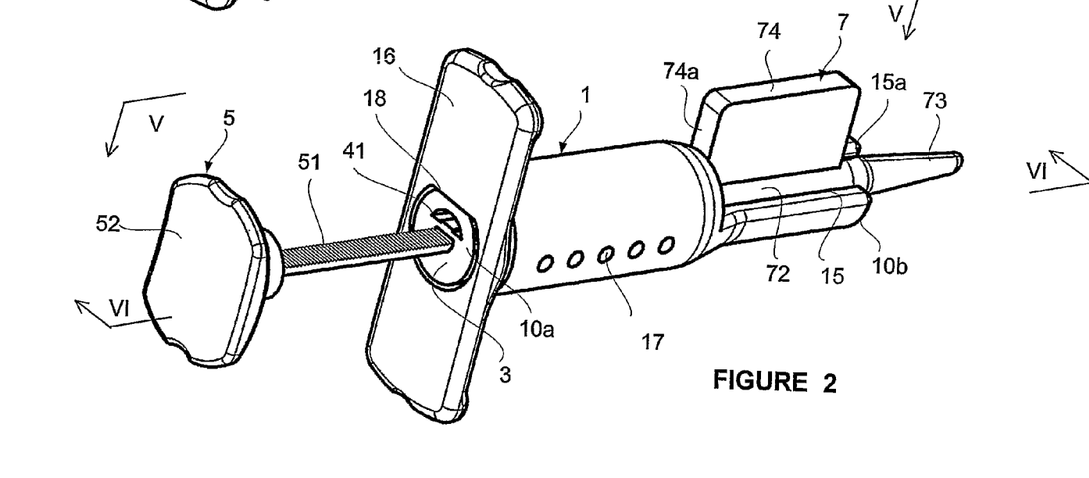
FIG. 2 is a view in perspective of the device of FIG. 1, equipped with an injection cartridge.
Figure 3:
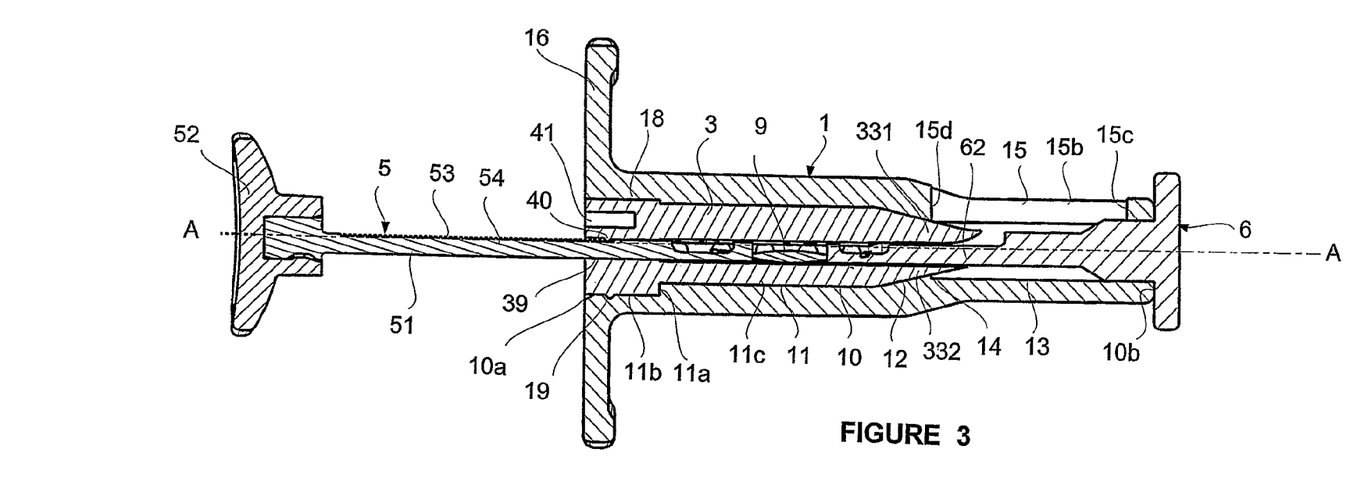
FIG. 3 is a view in longitudinal section along the plane III-III of the device of FIG. 1.
Figure 4:
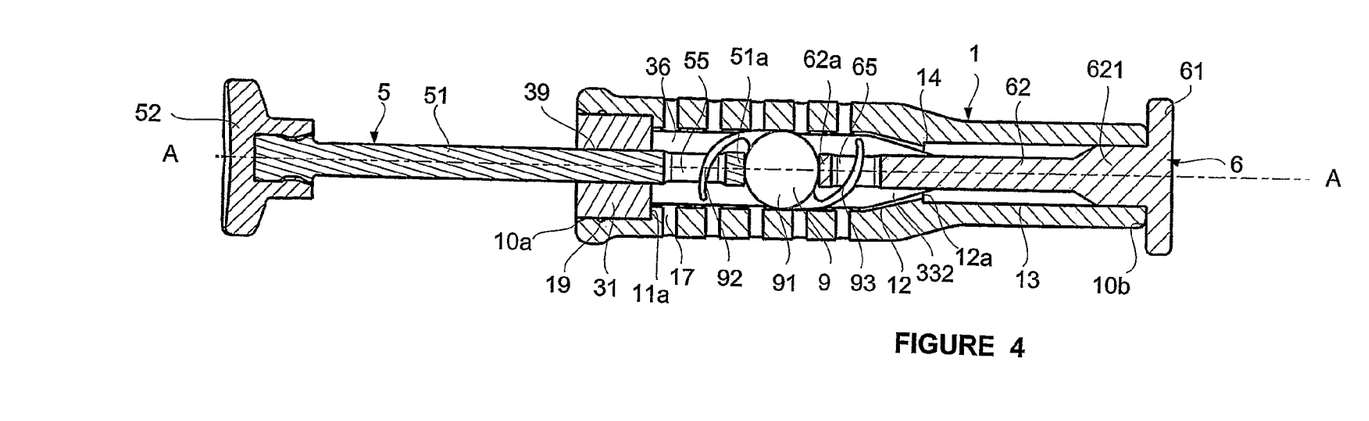
FIG. 4 is a view in longitudinal section along the plane IV-IV of the device of FIG. 1, illustrating the lower arm of the supporting element.

Referring to FIGS. 3 and 4, the internal passage 10 comprises the following, seen from its proximal end 10a to its distal end 10b: a first cylindrical section 11, called a receiving section, to receive a lens 9 in the deployed or unfolded state, this section 11 being extended by a second truncated section 12, called a folding section, whose internal diameter gets reduced towards the distal end up to a small-diameter outlet hole 12a, this folding section leading into a third end cylindrical section 13, designed to receive an injection cartridge. The diameter of this end section is greater than the diameter of the outlet hole 12a, the folding section and the end section thus defining a shoulder 14. The internal wall of the receiving section has a shoulder 11a oriented toward the proximal end 10a, separating the receiving section into a first large-diameter part 11b and a second small-diameter part 11c.

The tubular element has a bayonet-type longitudinal slot 15 used to join on a holding endpiece, also called a holding plug, or a cartridge as described here below. According to FIGS. 1 to 3, the slot 15 has a first part 15a which starts from the distal end 10b and is then extended by a second part 15b, this second part extending over an angle sector that is greater than the first part to define a retaining stop 15c. This slot extends across the entire length of the end section 13, as well as on a part of the folding section, thus eliminating the shoulder 14 on a sector corresponding to that of the second part of the slot. Two diametrically opposite legs 16, extending radially outwards, are provided on the outer wall of the tubular element, on its proximal end 10a side, to form pushing surfaces to actuate the plunger.

Figures 9, 10, 11, 12:
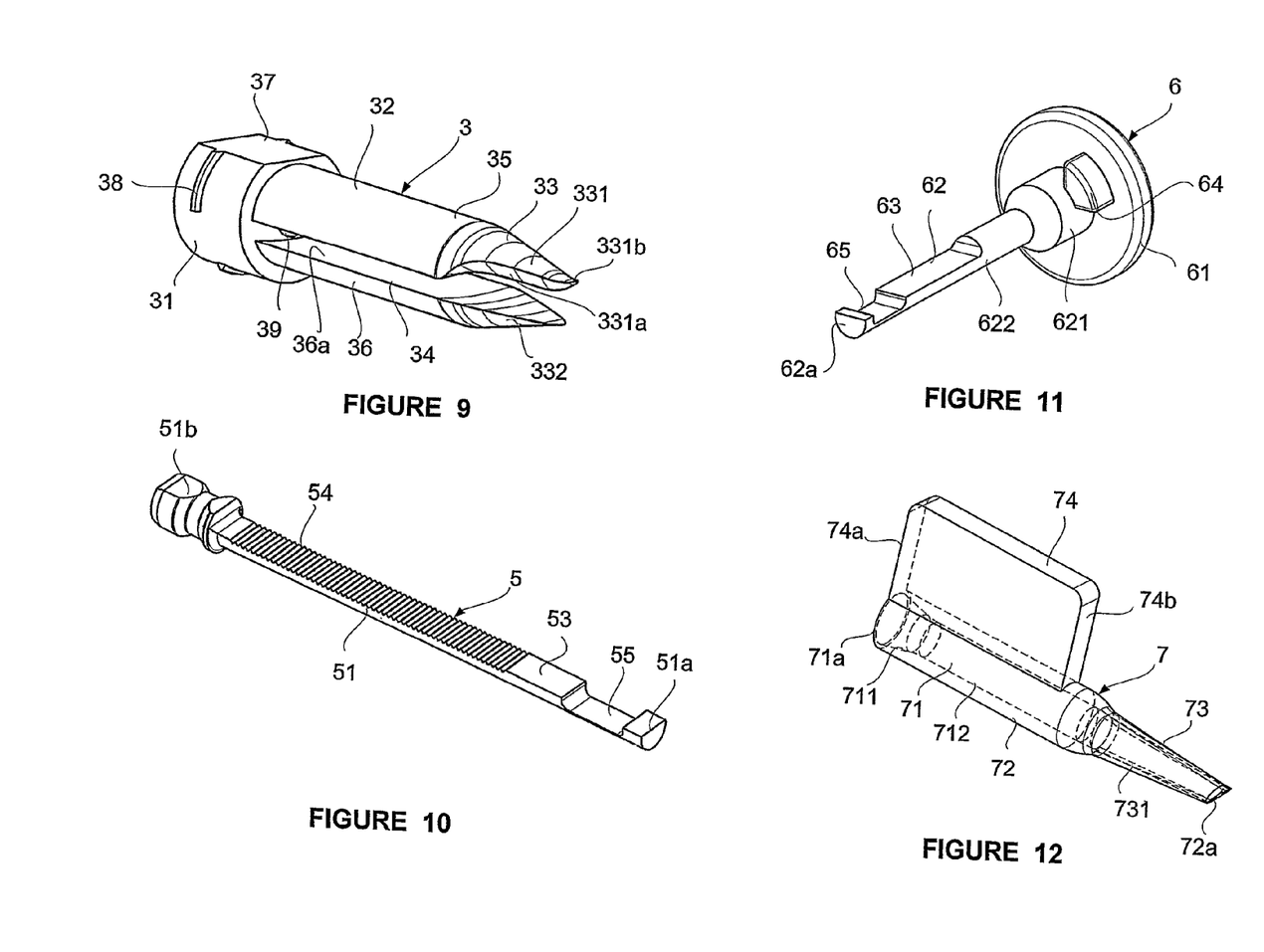
Figure 13:
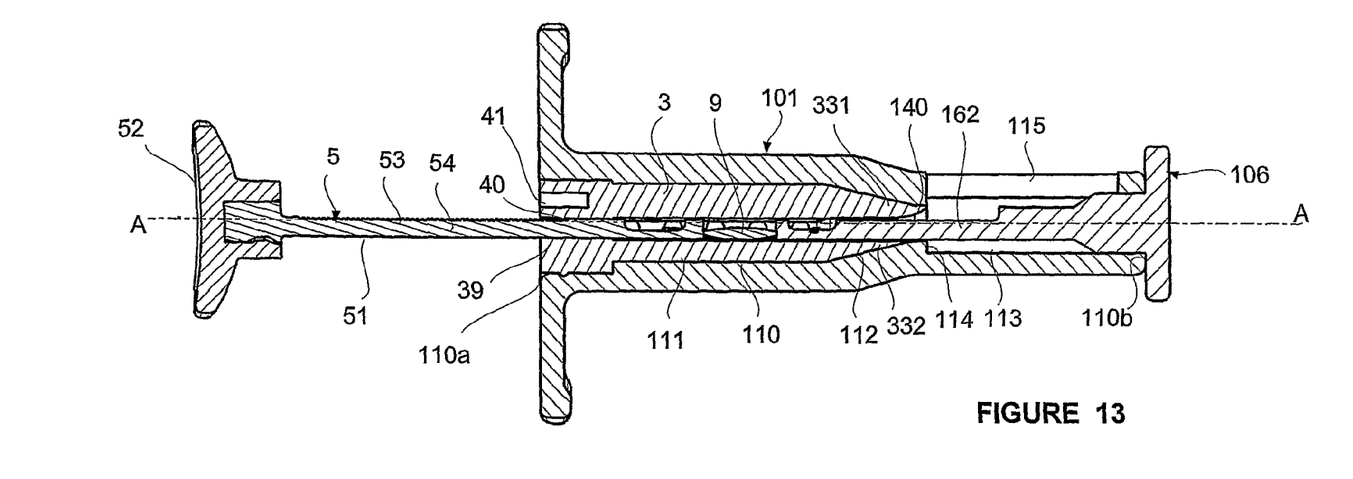
FIGS. 13 and 14 are views in section similar to those of FIGS. 3 and 4, illustrating a device according to an alternative embodiment equipped with an endpiece; and, FIGS. 15 and 16 are views in section similar to those of FIGS. 5 and 6, illustrating the device of FIGS. 13 and 14 equipped with an injection cartridge.
Figure 14:
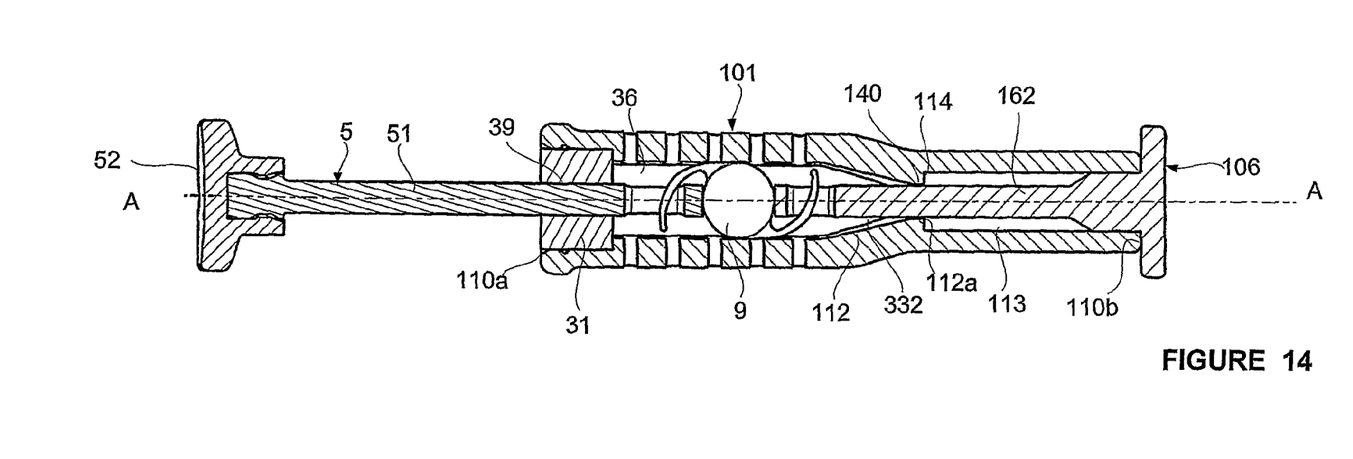

According to FIG. 9, the supporting element 3, designed to support the lens in a non-folded state, is formed by a split tip or split punch element, comprising a cylindrical head and a conical end, whose external end matches the receiving section and the folding section. Referring to FIG. 9, the support element 3 has a cylindrical head or base 31 whose external diameter substantially corresponds to the internal diameter of the first part 11b of the receiving section, and a tip comprising a cylindrical part 32 whose diameter substantially corresponds to the internal diameter of the second part 11c, extended by a conical part 33. A longitudinal slot 34, which is offset relative to the longitudinal axis of the supporting element, extends across the entire length of the tip to define an arm called an upper arm 35 and an arm called a lower arm 36.

Figure 7:
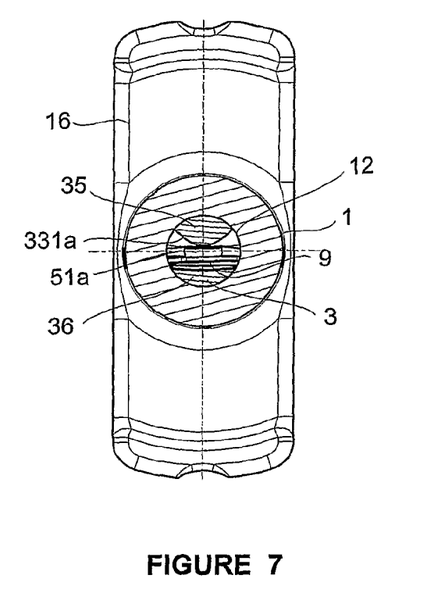
FIGS. 7 and 8 are respectively cross-section views along the section planes VII-VII and VIII-VIII of FIG. 5.

Referring to FIGS. 3, 4 and 7, when the supporting element is inserted into the tubular element, the conical parts 331, 332 of the arms come into contact by their external face with the truncated wall of the folding arm and extend beyond the outlet hole 12a in the end section 13. The face 36a of the lower arm, opposite the upper arm, on which the lens will be positioned, is slightly concave throughout its length. The lateral ridges of the conical part 331 of the upper arm 35 are rounded to form a convex guiding face 331a opposite the lower arm to guide the folding of the lens. This convex guiding face rises symmetrically up to the end 331b of the upper arm, and does so in the direction opposite that of the lower arm.

The blocking, in rotation, of the supporting element in the tubular element is obtained by a flat surface 37 formed on the external wall of the base 31 which co-operates with a flat surface 18 made in the internal wall of the first part 11b of the receiving section. A flange 38 (FIG. 9), which may be discontinuous for example, is provided on the external cylindrical wall of the base to get housed in a corresponding ring-shaped groove 19 of the first part 11b in order to lock the supporting element in translation in the tubular element. Side holes 17, arranged in two diametrically opposite sets are made in the wall of the tubular element. These holes open into the receiving section between the two arms of the supporting element.

Referring especially to FIGS. 3 and 10, the plunger 5 has a cylindrical rod 51 provided, at its proximal end 51b, having the widest cross-section, with an operating button 52 for its actuation. The rod has a flat surface 53 and is capable of getting inserted into a channel 39 of the base that opens out between the two arms. The flat surface has crosswise grooves 54 co-operating with a rib 40 formed on the flat surface 39a (FIG. 1) of the channel 39 of the base. The base has a weakening recess 41, for example with a generally semi-circular cross-section, that extends in parallel above the flat surface so that the rib can get elastically deformed and thus enable the plunger to be shifted inwards.

As can be seen in FIG. 11, the holding endpiece 6 has a disk 61 bearing an axial rod 62 capable of getting inserted into the tubular element by its distal end to achieve the longitudinal blocking, against the free end of the plunger rod, of the lens placed between the two arms. The rod has a first part 621 whose diameter corresponds to that of the end section 13 to secure the endpiece axially on the tubular element which is extended by a second part 622 having a diameter smaller than the diameter of the outlet hole 12a. This second part has a flat surface 63 to enable its insertion between the two arms, with its cylindrical wall against the concave face 36a of the lower arm, and its flat surface facing the upper arm 35. The endpiece is locked in rotation by a circular-sector pin 64 provided on the first part of the rod which gets housed in the first part 15a of the slot. The endpiece is held on the tubular element by the fitting of the first part 621 of the rod and of the pin respectively into the internal passage 10 and into the slot 15.

To receive a lens 9 having an optical part 91 and a haptic part constituted, for example, by two lateral hooks 92, 93, as illustrated in FIG. 4, the flat surface 53 of the rod 51 of the plunger has a transversal recess 55 near the free end 51a. This transversal recess 55 is designed to receive one of the hooks. In the vicinity of the free end 62a, the flat surface of the rod 62 of the endpiece has a transversal recess 65 to receive the other hook.

FIG. 12 shows a single-piece injection cartridge, without movable flaps, that can be used with the above-described loading device. The cartridge has a receiving chamber 71 for receiving the lens in folded form. This lens is formed by a single tube 72, extended by a cannula 73 for the injection of the folded lens. The receiving chamber has a truncated section 711 delimited on one side by the inlet hole 71a of the receiving chamber and extended on the other side by a cylindrical section 712. The cannula 73 has an internal channel 731 positioned in the extension of the cylindrical section 712 and having an internal diameter that gradually gets reduced toward the distal end 72a of this cannula. The distal end is advantageously bevelled to facilitate the insertion of the cannula into the eye. On its external wall, the tube has a rectangular, longitudinal flap 74 extending radially outwards.

A description shall now be made of the use of the device according to the invention.

At the first stage, the rod 51 of the plunger 5 is inserted into the channel 39 of the supporting element until its free end 51a is positioned between the two arms 35, 36, as illustrated in FIGS. 3 and 4. An intraocular lens 9 comprising, for example, an optical part 91 and two hooks 92, 93, is positioned between the two arms of the supporting element, on the concave face of the lower arm, against the free end 51a of the rod of the plunger, one of its hooks, the hook 92, being brought into the recess 55 of the rod. The supporting element is then inserted into the tubular element. Its base 31 abuts the shoulder 11a and the flange 38 gets clipped into the ring-shaped groove 19. The holding endpiece 6, held by its disk 61, is then inserted into the tubular element through the distal end. Its disk abuts the distal end and the free end of the rod comes against the optical part 91 of the lens. Before the full insertion of the endpiece or once this insertion has been made, the second hook 93 of the lens is brought into the recess 65 of the rod of the endpiece by means of an appropriate tool, such as a set of micro-pincers inserted through one of the side holes 17.

After a sterilizing operation, using a sterilizing agent passing through the side holes, the device thus pre-charged with a lens may be placed in a sterile pouch for storage, transportation and commercial distribution. The lens in the non-folded state is held radially between the two arms and the cylindrical wall of the second part 11c of the receiving section is held longitudinally between the free ends of the rod of the removable endpiece and the rod of the plunger button. The notches 54 on the rod of the plunger co-operating with the rib 40 enabling precise positioning of the plunger relative to the endpiece for optimum longitudinal securing of the lens.

Figure 5:
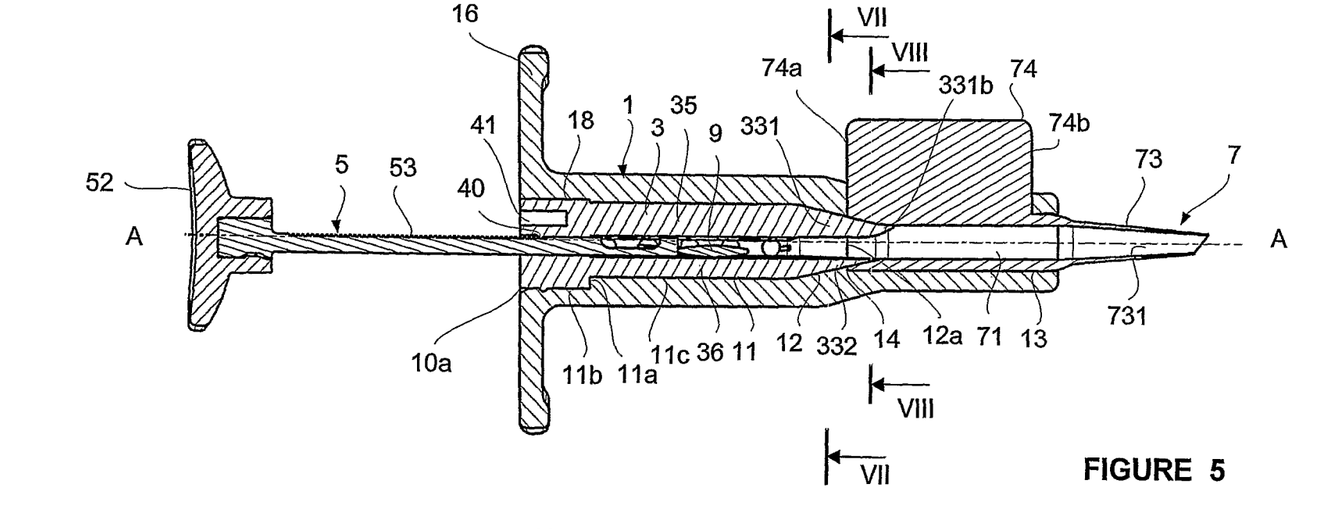
FIG. 5 is a view in longitudinal section along the plane V-V of the device of FIG. 2.
Figure 6:
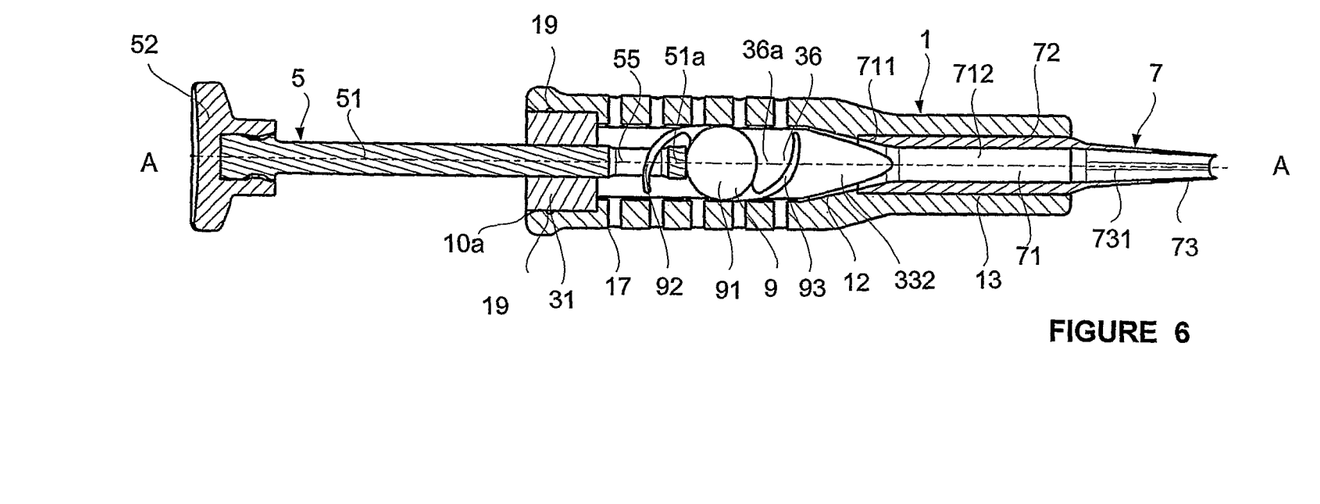
FIG. 6 is a view in longitudinal section along the plane VI-VI of FIG. 2, illustrating the lower arm of the supporting element.
Figure 8:
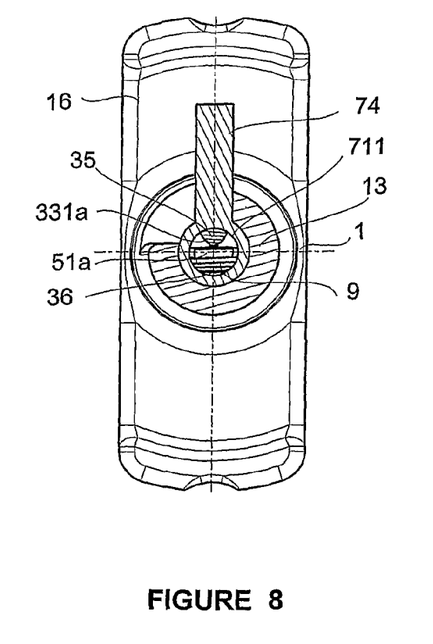

For the loading of the lens into an injection cartridge, the endpiece is removed from the tubular element and replaced by an injection cartridge. When the removable endpiece is withdrawn, the second hook placed in the recess of the lens is withdrawn frontward. The cartridge is inserted into the tubular element by the slot until the end of the tube 72 defining the inlet hole 71a of the receiving chamber abuts the shoulder 14, and the flap, by its rear edge 74a, abuts the rear end 15d (FIG. 3) of the slot. The cartridge is then made to pivot by about 45° to engage the flap in the second part 15b of the slot, with its edge 74b against the retaining stop 15c. In this position of the cartridge, the conical parts 331, 332 of the lower and upper arms extend in the truncated section 711 of the receiving chamber. As can be seen in FIGS. 5, 6 and 8, the lower part of the cylindrical wall defining the cylindrical section 712 of the receiving chamber is positioned in the extension of the concave face of the lower arm. As can be seen in FIG. 5, the end 331b of the upper arm gets positioned in the cylindrical section 712 of the chamber, with its external face against the wall of the cylindrical chamber.

The practitioner can then introduce the lens mechanically into the injection cartridge by actuating the plunger. During the forward movement of the plunger, the lens is pushed by the free end of the plunger into the receiving chamber. The lens, which moves along the concave face of the lower arm, presses laterally against the truncated wall of the folding section, gradually gets rolled up and then gets housed in the receiving chamber, the symmetrical convex guiding face guiding this gradual rolling-up process by holding the lens against the concave face of the lower arm during the rolling or folding process. The cartridge thus loaded with its lens can then be withdrawn from the loading device and positioned in a classic injector for insertion into the eyes by a small incision. The practitioner can then introduce lubricants, such as a saline solution or a viscoelastic agent into the device through side holes 17 and/or into the cartridge before it is positioned in the device, in order to facilitate the thrusting action and operation in which the lens is folded into its injection cartridge. Advantageously, the means for retaining the rod of the plunger in the channel of the base, constituted by the notches 54 and the rib 40, are shaped so as to form a no-return system prohibiting the withdrawal of the plunger out of the tube element, and hence any reuse of the loading device.

The dimensions of the loading device according to the invention, especially the dimensions of its internal passage and its supporting element, as well as the length of the rod of the holding endpiece, will be adapted to a given type of lens, depending especially on the size of its optical part, as well as the size, shape and arrangement of its haptic part as the case may be, to enable longitudinal and radial securing and then the gradual folding of the lens. Loading devices having different sizes could thus be proposed for the different types of lenses currently in the market. Furthermore, the convexity of the guiding face 331a will be adapted to the different types of lens which may be symmetrical or asymmetrical, continuous or variable.

Figure 15:
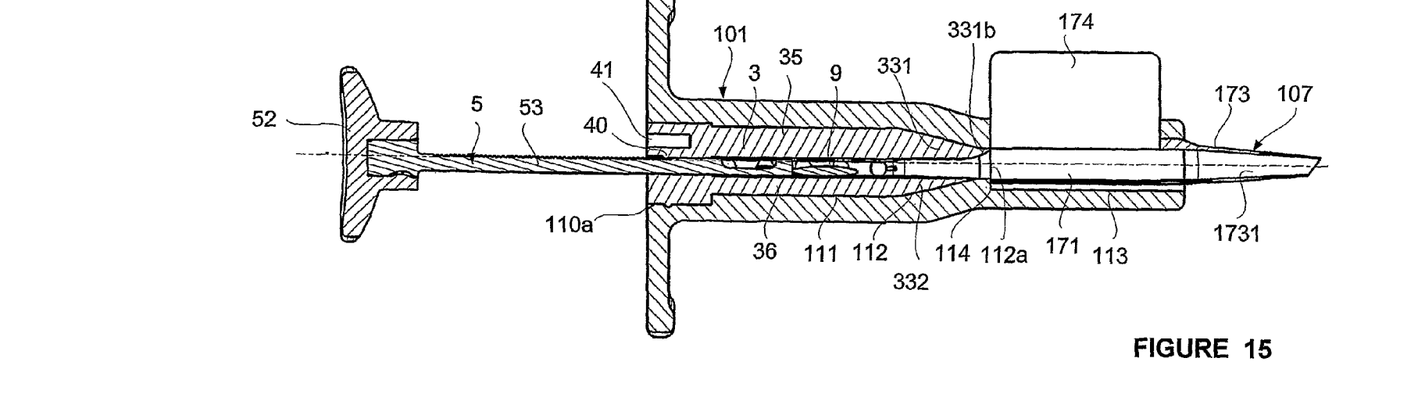
Figure 16:
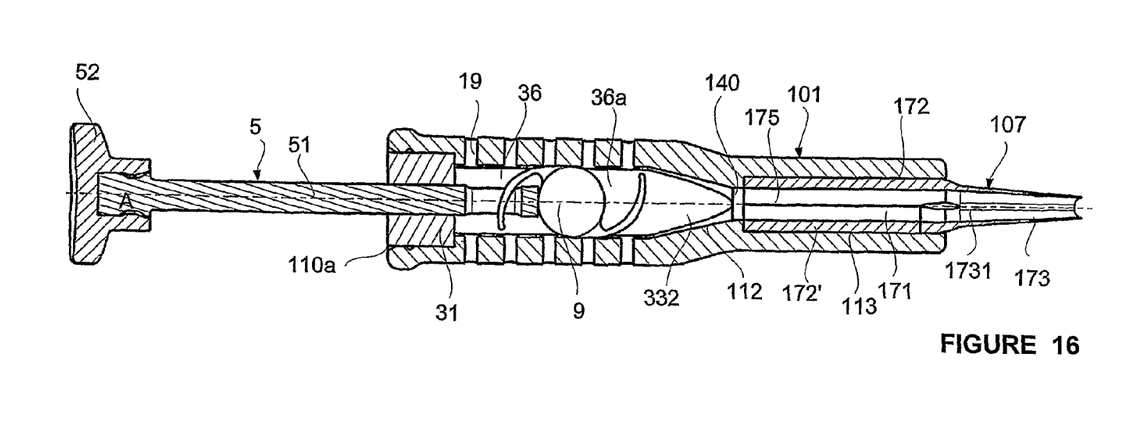

FIGS. 13 to 16 illustrate a loading device in an alternative embodiment, which can be used with a classic cartridge having mobile flaps. Referring to FIGS. 15 and 16, an injection cartridge, called a classic cartridge 107, has a cylindrical receiving chamber 171 extended by a cannula 173, the receiving chamber being formed by two half tubes 172, 172' of semi-circular section, joined by a hinge-forming linking line 175, each tube being provided with a flap 174 for shutting and opening the chamber.

In this variant, the conical parts 331, 332 of the supporting element do not extend into the receiving chamber of the cartridge. The supporting element 3 and the plunger 5 are identical to those described here above. The device differs from the one described here above by the fact that the internal passage 110 of the tubular element 101 has a second truncated folding section 112 of greater length to receive the totality of the conical parts 331, 332 of the two arms, with the exception of the curved end 331b of the upper arm, the truncated section being extended by a cylindrical intermediate section 140 whose outlet hole 112a opens out into the end section 113, said curved end being placed in this section 140. The slot 115 extends from the distal end 110b of the internal passage up to the shoulder 114. Furthermore, the endpiece 106 also has a rod 162, with a length slightly greater than that described here above, is which gets housed in the receiving section 111 extending from the proximal end 110a to the folding section.

The cartridge is positioned on the device after the two flaps are brought closer to each other in order to close the injection chamber. After the lens in folded form has been loaded into the receiving chamber, the cartridge is removed from the device with the chamber being kept closed, and it is then loaded into a classic injector.

Although the invention has been described with reference to a particular embodiment, it is clear that it is in no way restricted to this embodiment and that it includes all the technical equivalents of the means described as well as their combinations, should these combinations fall within the scope of the invention.

The invention claimed is:

1. A device for the loading of a flexible intraocular lens into an injection cartridge having a receiving chamber for receiving a lens and a cannula, the device comprising:
    a tubular element having an internal passage, said passage comprising a receiving section for receiving the lens in a non-folded state;
    an intermediate truncated folding section and an end section capable of receiving the injection cartridge detachably, so that the truncated intermediate folding section leads into the receiving chamber of the injection cartridge;
    a supporting element mounted in said receiving section having a proximal portion sized to receive the lens in the non-folded state and a distal portion in contact with the lens and having at least an upper arm which defines a convex face extending distally along and within the intermediate truncated folding section; and
    a plunger comprising a rod that is mounted so as to be movable in the internal passage, capable of pushing the lens positioned in the receiving section through the truncated intermediate folding section to fold said lens gradually, then in the receiving chamber of the injection cartridge placed in the end section.

2. The device according to claim 1, comprising a braking mechanism formed of one or more projections along the rod of the plunger which create at least resistance to a rearward return of the rod of the plunger in said internal passage, said end section being capable of detachably receiving a holding mechanism that extends in the internal passage up to its receiving section to longitudinally block a lens positioned in said receiving section against the free end of the rod of the plunger.

3. The device according to claim 2, wherein said braking mechanism creates a blocking of the rearward return of the rod of the plunger in the internal passage and resistance to the forward movement of the rod of the plunger in the internal passage.

4. The device according to claim 2, wherein the holding mechanism includes an endpiece comprising a retaining rod sized to fit into the internal passage through the open distal end of said internal passage and into apposition against the lens.

5. The device according to claim 4 wherein the tubular element comprises side holes opening out into the receiving section to enable the passage of at least one of sterilizing agent, lubricants and a tool to position the haptic part of the lens relative to a rod of the holding endpiece.

6. The device according to claim 1, wherein the internal passage of the tubular element comprises an open distal end sized to receive the injection cartridge, the tubular element defining a longitudinal slot extending up to said distal end for receiving a flap of the injection cartridge.

7. The device according to claim 6, wherein the longitudinal slot is of a bayonet type which blocks the injection cartridge in the end section by engagement of the flap in the longitudinal slot.

8. The device according to claim 1, wherein the internal passage of the tubular element comprises an open proximal end by which the supporting element is fitted into the receiving section.

9. The device according to claim 8, wherein a tip of the supporting element has a conical end extending in the truncated folding section of the internal passage.

10. The device according to claim 9, wherein a slot defined along the tip is offset relative to the longitudinal axis of the tip.

11. The device according to claim 10, wherein the conical end extends in the end section of the tubular element and is sized for insertion in the truncated inlet section of the receiving chamber of an injection cartridge placed in said end section.

12. The device according to claim 9, wherein the conical end extends in the end section of the tubular element.

13. The device according to claim 8, wherein said end section is capable of detachably receiving a holding mechanism, wherein the holding mechanism includes an endpiece comprising a retaining rod sized to fit into the internal passage through the open distal end of said internal passage and into apposition against the lens.

14. The device according to claim 8, wherein the supporting, element comprises a tip with a head sized to fit into the receiving section, the tip defining a longitudinal slot between an upper arm and a lower arm into which a lens is fitted and which is also sized to translatably receive the rod.

15. The device according to claim 1, wherein the device is loaded with a flexible intraocular lens and packed in a sterile pouch.

16. The device according to claim 1, further comprising an injection cartridge designed to be loaded with a flexible intraocular lens the cartridge comprising a receiving chamber for receiving a lens in folded form extended by a cannula for the injection of the folded lens.

17. The device according to claim 16, wherein the receiving chamber has a truncated section delimited on one side by an inlet hole of the receiving chamber and extended on the other side by a cylindrical section.

18. The device according to claim 17, wherein said tube comprises, on its outer wall, a rectangular longitudinal flap extending radially outwards.

19. The device according to claim 16, wherein said tube comprises, on its outer wall, a rectangular longitudinal flap extending radially outwards.

20. The device according to claim 1, wherein a tip of said supporting element has a conical end extending in the truncated folding section of the internal passage, the supporting element further having a lower arm which defines a concave face opposing the convex face such that each face is shaped so as to form guiding surfaces for the folding of the lens.

21. The device according to claim 20, wherein a slot defined along the tip is offset relative to a longitudinal axis of the tip.

22. A set comprising a loading device according to claim 1 and an injection cartridge, comprising a reception chamber and a cannula.

* * * * *